United States Patent [19]
Applegate et al.

[11] Patent Number: 5,310,923
[45] Date of Patent: May 10, 1994

[54] PREPARATION OF HIGH PURITY THIABENDAZOLE

[75] Inventors: Lynn E. Applegate; Carl A. Renner, both of Wilmington, Del.

[73] Assignee: E. I. Du Pont de Nemours and Company, Wilmington, Del.

[21] Appl. No.: 55,437

[22] Filed: Apr. 30, 1993

[51] Int. Cl.$^5$ .................................. C07D 417/04
[52] U.S. Cl. .................................................. 548/181
[58] Field of Search ............................. 548/181, 310.7

[56] References Cited

FOREIGN PATENT DOCUMENTS

| 99787 | 8/1973 | Fed. Rep. of Germany | ...... 548/181 |
| 127931 | 10/1977 | Fed. Rep. of Germany | ...... 548/181 |

OTHER PUBLICATIONS

Hofmann, Imidazole pp. 260–267 (1953).
Katritzky, Comprehensive Heterocyclic Chemistry vol. 5 p. 470 (1984).
Sklyarova, Zh Org. Khim 22 645 (1980).
Tsuchiya, Chem Pham. Bull 35 2985 (1987).

*Primary Examiner*—Robert Gerstl
*Attorney, Agent, or Firm*—Charles E. Feeny

[57] ABSTRACT

Process for preparing 2-(4'-thiazolyl)-benzimidazole (generic name: thiabendazole) by the acid-catalyzed condensation of o-phenylenediamine and 4-cyanothiazole using as a solvent polar organic compounds in which the reactants, catalysts and impurities are soluble, and the product, thiabendazole, is substantially insoluble.

12 Claims, No Drawings

PREPARATION OF HIGH PURITY THIABENDAZOLE

FIELD OF THE INVENTION

The present invention relates to an improved process for preparing 2-(4'-thiazolyl)-benzimidazole (generic name: thiabendazole) by the acid-catalyzed condensation of o-phenylenediamine and 4-cyanothiazole using a polar organic solvent as the reaction medium.

BACKGROUND OF THE INVENTION

Thiabendazole gained commercial importance when Brown et al. (J. Am. Chem. Soc. 83, 1764 (1961)) reported that the compound prepared by reacting 4-thiazolecarboxamide with o-phenylenediamine using an acid catalyst, polyphosphoric acid, exhibits broad spectrum anthelmintic activity without adverse toxic effects. The reaction described by Brown is conducted at a temperature of 250° C. and results in a 64 per cent yield of thiabendazole. Thiabendazole continues to be extensively used for the treatment and/or prevention of helminthiasis in livestock. Thiabendazole is, also, a systemic fungicide widely used for pre/post harvest spoilage control of raw agricultural commodities.

Because of the commercial importance of thiabendazole, the chemical literature is replete with various other synthetic routes aimed toward producing this pharmacologically and fungicidally active compound in high yield and high purity. Prior art processes for preparing thiabendazole suffer from inherent drawbacks and inconveniences, such as low yields, additional purification steps, long reaction times, environmentally undesirable organic solvents and high pressure reaction conditions. Hence, it would be a significant improvement in the art, if thiabendazole could be efficiently prepared under mild conditions in high yield and in the purest possible form for agricultural and pharmaceutical use. It would also be an advantage, if thiabendazole could be prepared using a simple, one-step, environmentally friendly process which is easily adapted to commercial scale production.

SUMMARY OF THE INVENTION

The process of the present invention overcomes the disadvantages of prior processes by reacting o-phenylenediamine and 4-cyanothiazole at moderate temperatures in the presence of an acid catalyst using a liquid polar organic compound as the reaction medium. The process of this invention provides a high purity thiabendazole product in high yield and advantageously without the need for additional purification steps. In addition, it provides substantial environmental benefits by employing environmentally innocuous organic compounds as the reaction medium. Moreover, the mother liquor can be reused in whole or in part, or recovered for reuse by distillation, and solvent wash can be recycled to the reactor. Another advantage of the process of this invention is that the reaction is carried out under mild conditions, i.e., at nominal atmospheric pressure and at reaction temperatures typically below 145° C., and within a commercially feasible period of time.

DETAILED DESCRIPTION OF THE INVENTION

Surprisingly, it has been found in the process of this invention that a variety of acid catalysts, can be employed to carry out the condensation reaction in polar organic compounds in which thiabendazole is insoluble and in which the reactants, acid catalysts and impurities are soluble. It has been found particularly advantageous to carry out the acid-catalyzed condensation using hydrochloric acid as the acid catalyst and 1-butanol as the reaction medium.

Suitable polar organic compounds are those in which the reactants, catalysts and impurities are soluble, and the product, thiabendazole, is substantially insoluble. Suitable polar organic compounds include: lower alkanols containing 3 to 8 carbon atoms, e.g., 1-propanol, 1-butanol, 2-butanol, 2-methyl-1-propanol (isobutyl alcohol), 3-methyl-1-butanol (isoamyl alcohol), 2-ethyl-1-hexanol, cyclohexanol; dihydric alcohols containing 2 to 8 carbon atoms, e.g. 1,2-ethanediol, 1,2-propanediol, 1,3-propanediol, and 1,5-pentanediol; alkane polyethers containing 4 to 10 carbon atoms and 2 to 4 oxygen atoms, e.g., 1,4-dioxacyclohexane (dioxane), 1,1'-oxybis[2-methoxyethane] (diglyme), and 2,5,8,11-tetraoxadodecane (triglyme); and alkoxyalkanols containing 1 to 8 carbon atoms in the alkoxy group and in the alkanol portion of the molecule, e.g., those of the Cellosolve type: 2-methoxyethanol, and 2-ethoxyethanol. The preferred polar organic solvents are $C_4$ alkanols. The most preferred polar organic solvent is 1-butanol because colored impurities, compounds containing chromophoric groups, are solubilized.

Suitable acid catalysts which can be used to catalyze the reaction of this invention fall into several categories: hydrogen halides, which can be anhydrous or supplied as solutions, typically in water, e.g., hydrochloric acid, hydrobromic acid; ammonium salts, e.g., ammonium chloride, ammonium bromide, ammonium acetate, ammonium phosphate and ammonium nitrate; Lewis acids, e.g., zinc chloride, stannous chloride, aluminum chloride, etc; organic acids, e.g., acetic acid, oxalic acid, propionic acid, adipic acid, methanesulfonic acid, benzenesulfonic acid, p-toluenesulfonic acid and sulfamic acid. The only restriction with respect to the acid used is that the corresponding acid salt of o-phenylenediamine be soluble in the reaction medium used. In the case of Lewis acids the only restriction is that the Lewis acid and o-phenylenediamine be soluble in the reaction medium used. The preferred acid catalyst is hydrochloric acid because o-phenylenediamine monohydrochloride salt is soluble in all of the suitable solvents listed. In addition to this, hydrochloric acid is a low cost and readily available acid. The mole ratio of OPD to acid catalyst will depend upon the type of acid used.

The mole ratio of OPD to Lewis acid can range between
  Broadest: 1.0:0.01 and 1.0:0.1
  Preferred: 1.0:0.02 and 1.0:0.06.

The mole ratio of OPD to ammonium salt or sulfamic acid can range between
  Broadest: 1.0:0.1 and 1.0:0.5
  Preferred: 1.0:0.2 and 1.0:0.4.

The mole ratio of OPD to hydrogen halides or organic acids can range between
  Broadest: 1.0:0.1 and 1.0:1.0
  Preferred: 1.0:0.7 and 1.0:0.92.

The reaction will occur at temperatures of 85° C. and above. Below 85° C. the reaction proceeds too slowly to be practical. The reaction mixture should generally be maintained between about 85° C. and about 145° C. It is more practical to effect reaction at temperatures between about 90° C. and 140° C. With the preferred 1-butanol reaction medium, a temperature between 110° and 122° C. is preferred.

The mole ratio of o-phenylenediamine to 4-cyanothiazole can range between 1:0.9 and 1:1.1. For economic reasons it is undesirable for one of the reactants to be present in large excess. Therefore, the preferred mole ratio of o-phenylenediamine to 4-cyanothiazole is 1:0.95 to 1:1.05, which allows efficient use of the reactants.

The thiabendazole product is substantially insoluble in the reaction media used and therefore precipitates as it is formed. The target product is recovered by cooling the reaction mass to about 25° C., filtering, washing with fresh solvent corresponding to that used as the reaction medium, followed by, deionized water to remove the ammonium acid salt or the Lewis acid. The wet thiabendazole cake is dried in a vacuum oven.

The purity of thiabendazole prepared using the present process as determined by High Performance Liquid Chromatography (HPLC) is typically 99.9% (based on area %). This level of purity is significantly higher when compared with commercially available thiabendazole with an HPLC analyzed purity ranging between 99.0% and 99.5% (based on area %). In addition, the purity of thiabendazole prepared using the present process as determined by Gas Chromatography (GC) is typically 99.8% (based on area %). Again, this level of purity is significantly higher when compared with commercially available thiabendazole with a GC analyzed purity of 99.2% (based on area %).

In a preferred embodiment, the process comprises contacting one equivalent of o-phenylenediamine, preferably a 3%-10% stoichiometric excess, with less than one equivalent of hydrochloric acid in a $C_4$ alkanol, most preferably 1-butanol, thereby effecting formation of the o-phenylenediamine monohydrochloride salt. In order to raise the reflux temperature of the reaction mixture and correspondingly increase the rate of reaction, a portion of the 1-butanol+water can be removed by distillation. When carrying out the distillation phase the amount of 1-butanol+water removed vs the amount of 1-butanol added can range between Broadest: 0.25 and 0.70
Preferred: 0.40 and 0.65.

One equivalent of 4-cyanothiazole is added after approximately half of the desired volume of 1-butanol+water has been removed. The reaction is carried out at nominal atmospheric pressure and at a reflux temperature ranging between 110° and 122° C. for a period of time ranging between 3 hours and 12 hours, preferably 4 hours and 6 hours. The product is isolated from the mother liquor (comprising impurities and unreacted starting materials) by filtering and washing with fresh $C_4$ alkanol and then water. The white solid thiabendazole product is prepared in greater than 88% yield and with 99.9% purity as determined by HPLC. At nominal atmospheric pressure, the reaction time will depend upon the concentration of starting material (i.e., o-phenylenediamine and 4-cyanothiazole), the molar equivalents of HCl, and the reflux temperature of the system. When the reaction conditions described in Example 1 were employed, the reaction was complete within 6 hours which is a relatively short period of time compared with prior art processes.

In general in a typical embodiment of the process of this invention, a suitable reaction vessel is charged with a polar organic compound, such as 1-butanol. Because o-phenylenediamine is sensitive to dissolved oxygen in organic solvents, an oxidation inhibitor (antioxidant) such as ascorbic acid, may be added prior to adding o-phenylenediamine. The system is purged with nitrogen to remove air and a nitrogen sweep is maintained for the duration of the reaction. The agitator is started and sufficient stirring is maintained for the duration of the reaction. At least a stoichiometric amount of o-phenylenediamine (in flake or granular form or as a melt), or a salt thereof, preferably 3% to 10% above stoichiometry, is charged to the reaction vessel. (It has been demonstrated that a slight molar excess of o-phenylenediamine corresponding to 3% to 10% improves the yield of thiabendazole. The temperature of the reaction medium to which o-phenylenediamine is added can range between about 25° C. up to about 95° C.) An acid catalyst, such as hydrochloric acid, in an amount ranging between 23% and 97% of the theoretical amount needed to neutralize the ammonia generated, is added in a controlled manner to form a slurry containing o-phenylenediamine monohydrochloride salt. The reaction mixture is heated, and when the pot temperature is about 70° C., all of the o-phenylenediamine, or a salt thereof, is in solution. A portion of the volume of 1-butanol+water is distilled off to remove a portion of water from the reaction mixture. This allows the reflux temperature of the system to rise from 101° C. to a maximum temperature of 122° C., thereby increasing the rate of the reaction. A stoichiometric amount of solid or molten 4-cyanothiazole is charged to the reaction vessel and a water scrubber is added to the exit of the condenser. (The concentration of starting materials in the reaction mixture can range between Broadest: 1.25 moles/l and 5.4 moles/l of solvent
Preferred: 2.0 moles/l and 3.0 moles/l of solvent.

Above a concentration of 5.4 moles/l, the reaction mixture containing the solid thiabendazole product will be too thick and therefore difficult to stir. Below a concentration of 1.25 moles/l, the reaction rate will be too slow to be practical. In order to assure an efficient and economic process high concentrations will usually be chosen). The reaction mixture is refluxed for a period of 4–6 hours (reflux temp. ranges between 122°–115° C. at the start of the reaction and gradually decreases during the course of the reaction). Since thiabendazole is only slightly soluble in 1-butanol, the product precipitates as it is formed in the reaction mixture. Upon completion of the reaction, the reaction mixture is cooled to room temperature.

To isolate the product, a sufficient amount of 1-butanol may be added to thin the reaction mixture before the solid product is separated from the mother liquor by vacuum filtration. The filter cake is washed with portions of fresh 1-butanol to remove solubilized impurities, and then with portions of deionized water until the filtrate gives a negative test for chloride ion (using $AgNO_3$ solution which indicates the ammonium chloride coproduct is removed). The solid thiabendazole product is then dried in a vacuum over under 15 to 20″ Hg and at a temperature of 80°–85° C.

The reaction may be monitored by gas chromatography for the disappearance of peaks corresponding to o-phenylenediamine and 4-cyanothiazole. Procedure is as follows: dissolve a sample of the reaction mixture in an organic solvent, e.g., DMAC, acetonitrile or methanol; filter solids and inject into the gas chromatograph.

The point at which 4-cyanothiazole is added is not critical to the success of this process. Hence, 4-cyanothiazole can be added before o-phenylenediamine, before catalyst addition, prior to distillation or as in Example 1, after removing a portion of 1-butanol+water. Addition of HCl can be carried out when the reaction mixture is at room temperature or at a temperature of about 65° to about 95° C. While not considered a preferred method, hydrochloric acid can be added during the reaction of o-phenylenediamine and HCl in sufficient proportion to adjust the pH of a mixture (at or above room temperature) of o-phenylenediamine in 1-butanol to an "apparent" value ranging between 2.5 and 6.0. Typically, 4-cyanothiazole is added next and the reaction mixture is heated to reflux (101°-104° C.). During the course of the reaction, the "apparent" pH is maintained within +/−0.2 of the desired value by periodic addition of hydrochloric acid. When this technique is used, 4-cyanothiazole may be added to the reaction vessel without first removing a portion of the polar organic compound and water as described above. As a practical matter pH values which are obtained in a virtually anhydrous medium may not reflect the true hydrogen ion concentration. However, it is still possible to obtain what is referred to as "apparent" pH values in anhydrous media which reflect changes in acid strength in the medium. Thus, for each individual anhydrous reaction medium suitable for the present process, it is possible to establish through experimentation the ranges of preferred pH values. When anhydrous acids are employed, it will not be necessary to carry out the distillation step.

Although the addition of a trace amount of an antioxidant such as ascorbic acid, is not essential to the success of this process, an antioxidant may be added to avoid negligible amounts of colored impurities in the final product. Colored impurities, compounds containing chromophoric groups, may be present when o-phenylenediamine can not be scrupulously protected from exposure to air.

The concentration of an antioxidant, such as ascorbic acid, in the reaction mixture can range between Broadest: 0 mole/l and $9 \times 10-3$ mole/l
Preferred: $3.1 \times 10-3$ mole/l and $5.7 \times 10-3$ mole/l.

EXAMPLES

EXAMPLE 1

To a 500 ml four-neck, round-bottom flask fitted with a mechanical stirrer, thermometer with $N_2$ inlet and a condenser equipped with a Dean-Stark trap were charged 285 ml of 1-butanol and 0.1 g ($5.7 \times 10-4$ mole) of ascorbic acid. The entire assembly was flushed with $N_2$ by introducing $N_2$ at the thermometer inlet and allowing $N_2$ to exit at the top of the condenser. After flushing, a $N_2$ sweep was maintained on the system for the duration of the reaction. Subsequently, 54 g (0.5 mole) of o-phenylenediamine were charged to the reaction vessel, followed by, dropwise addition of 41.5 ml (0.42 mole HCl) of 20 degree Be' hydrochloric acid (corresponding to 32.2% hydrogen chloride) over a period of about 30 minutes. During the addition of hydrochloric acid, the temperature of the reaction mixture increased from room temperature to 35° C., as a slurry of o-phenylenediamine monohydrochloride salt formed. The mixture was heated to distill off 130 ml of 1-butanol+water.

When the pot temperature reached about 70° C., all of the o-phenylenediamine monohydrochloride salt was in solution. When half (~65 ml) of the 1-butanol+water has been distilled, 55 g (0.5 mole) of 4-cyanothiazole were added to the reaction flask and a water scrubber (200 ml of water) was added to the exit of the condenser. After a total of 130 ml of 1-butanol+water was distilled, which took about 40 minutes, the Dean-Stark trap was removed from the system. During the removal of 1-butanol+water, the temperature of the reaction mixture rose to 115° C.

As the reaction progressed the reflux temperature gradually decreased to 110° C. from an initial reflux temperature of 115° C. Thiabendazole formed during refluxing as a precipitate. The reaction was monitored by gas chromatography and determined to be complete when the peaks corresponding to o-phenylenediamine and 4-cyanothiazole were negligible. After 6 hours of reflux, the reaction mass was cooled to room temperature and 40 ml of 1-butanol were added to thin the mixture. The mixture was filtered to collect the precipitate using a Buchner funnel and #4 Whatman filter paper. The precipitate was washed with two 100 ml portions of 1-butanol and then washed with three 300 ml portions of deionized water at room temperature. The third water wash gave a negative test for chloride ion using $AgNO_3$ solution. The wet cake was dried overnight in a vacuum oven under 15-20" Hg and at a temperature of 80°-85° C. Thiabendazole was obtained in the form of white crystals and weighed 88.97 g, which corresponds to a yield of 88.5%. The purity was determined to be 99.88% (based on area %) using a Hewlett-Packard Model 1090M High Performance Liquid Chromatograph.

EXAMPLE 2

The same procedure as that described in Example 1 was carried out with the exception that the reaction was run for 4 hours. Yield was 87.0%, and purity was the same as in Example 1.

EXAMPLE 3

The same procedure as that described in Example 1 was carried out with the exception that 90 ml of 1-butanol+water were distilled before 4-cyanothiazole was added, followed by 50 ml of 1-butanol. After a total of 180 ml of 1-butanol+water was distilled, the Dean-Stark trap was removed from the system. During the removal of 1-butanol+water, the temperature of the reaction mixture rose to 122° C. During the refluxing phase, the concentration of the starting material, o-phenylenediamine (2.66 moles/l), 4-cyanothiazole (2.66 moles/l), and HCl (0.85 molar equivalents based on o-phenylenediamine) was the same as in Example 1, however the initial reflux temperature was 122° C. and gradually dropped to 116° C. The reaction was determined to be complete after 4 hours. Yield was 88.4% and purity 99.8%. In Example 3, the increase in yield of 1.4% (absolute) compared with Example 2 is believed to be caused by the reaction taking place at a higher reflux temperature as a result of more water having been removed during the distillation phase.

EXAMPLES 4-8

The same procedure as that described in Example 1 was carried out with the exception that the amount of HCL added varied.

TABLE I

Amount of HCl Added And Effect On the Yield And Purity of Thiabendazole

| Ex. # | HCl (ml) | HCL (mole) | Mole Ratio (OPD:HCl) | % Yield | % Purity (HPLC area %) | Color |
|---|---|---|---|---|---|---|
| 4 | 23.0 | 0.230 | 1:0.46 | 89.8 | 99.85 | Sl. Yel. |
| 5 | 36.8 | 0.369 | 1:0.74 | 88.5 | 99.88 | White |
| 1 | 41.51 | 0.412 | 1:0.85 | 88.5 | 99.88 | White |
| 6 | 46.0 | 0.459 | 1:0.92 | 88.6 | 99.87 | White |
| 7 | 48.5 | 0.486 | 1:0.97 | 79.6 | 99.88 | White (Yellow Tint) |
| 8 | 50.5 | 0.504 | 1:1.00 | 53.8 | 99.80 | White (Yellow Tint) |

Conclusion: As the molar equivalents of HCl used decreases, the rate of reaction increases. The color of the isolated thiabendazole product is a function of the molar equivalents of HCl used. The optimum whiteness is achieved when the molar equivalents of HCl are greater than 0.46 and less than 0.97 based on o-phenylenediamine (OPD).

EXAMPLES 9-13

The same procedure as that described in Example 1 was carried out with the exception that 46 ml of HCl were added in Examples 9-11 and the reaction time was 8 hours for all runs.

TABLE II

Effect of Using a Stoichiometric Excess of One Reactant on the Yield of Thiabendazole

| Ex. # | HCL (ml) | Mole Ratio (OPD:4-CNT) | Rxn Time (hrs) | % Yield | % Purity (HPLC area %) | Color |
|---|---|---|---|---|---|---|
| 9 | 46 | 1.00:1.00 | 8.0 | 88.0 | 99.87 | White (Orange Tint) |
| 10 | 46 | 1.00:1.00 | 8.0 | 88.0 | 99.84 | slightly Yellow |
| 11 | 46 | 1.10:1.00 | 8.0 | 90.0 | 99.85 | White |
| 12 | 41.5 | 1.03:1.00 | 8.0 | 90.0 | 99.83 | White |
| 13 | 41.5 | 1.03:1.00a | 8.0 | 92.3 | 99.84 | White | a A 3% stoichiometric excess of o-phenylenediamine (OPD) and reaction medium comprises the combined first and second 1-butanol washes from Example 12 + 95 ml of fresh 1-butanol.

Conclusion: A 3%-10% stoichiometric excess of o-phenylenediamine increases the yield of thiabendazole. The yield of thiabendazole can be further increased without adversely affecting the purity of thiabendazole by recycling the 1-butanol wash.

EXAMPLE 14

The same procedure as that described in Example 1 was carried out by replacing 1-butanol with the polar solvents listed in Table III. At the same concentration of starting material and molar equivalents of HCl, the reaction time depends upon the reflux temperature, therefore higher boiling solvents required shorter reaction times.

TABLE III

Synthesis of Thiabendazole in Other Polar Solvents

| Solvent | Reflex Ti (°C.) | Reflux Tf (°C.) | Rxn Time (hrs) | % Yield | % Purity (HPLC area %) |
|---|---|---|---|---|---|
| 2-Butanol | 100 | 92 | 12.0 | 90.4 | 99.8 |
| 2-Methoxyethanol | 128 | 121 | 6.0 | 81.8 | 99.8 |
| 3-Methyl-1-Butanol | 139 | 131 | 3.5 | 85.3 | 99.8 |
| 2-Methyl-1-Propanol | 106 | 102 | 8.0 | 87.0 | 99.7 |

EXAMPLE 15

Synthesis of thiabendazole in ethylene glycol at a reaction temperature ranging between 125°-130° C.

To a 500 ml four-neck, round-bottom flask fitted with a mechanical stirrer, thermometer with $N_2$ inlet and a distillation take-off condenser were charged 200 ml of ethylene glycol. The reaction vessel was purged with nitrogen and then nitrogen blanketed for the duration of the reaction. Next, 27 g (0.25 mole) of o-phenylenediamine, followed by 15 ml (0.12 moles) of concentrated hydrochloric acid (corresponding to 38% hydrogen chloride) were added and a rapid 8° C. rise in the temperature of the mixture was observed. This rise in temperature resulted from the exothermic acid-base reaction in which o-phenylenediamine was converted to o-phenylenediamine monohydrochloride salt.

The mixture was heated and when the pot temperature reached 164° C., distillation commenced. The temperature gradually increased to 201° C. and a total of 44 ml of water plus ethylene glycol distillate were removed. The mixture was allowed to cool to 100° C. before 27.5 g (0.25 moles) of 4-cyanothiazole were added to the solution containing o-phenylenediamine monohydrochloride. The reaction mixture was heated to 125° C. and held within a temperature range of 125°-130° C. for a period of 5 hours. Thiabendazole formed as a precipitte during the 5 hours of heating.

The reaction was monitored by gas chromatography and determined to be complete when the peaks corresponding to o-phenylenediamine and 4-cyanothiazole were negligible. Next, the reaction mass was cooled to 50° C. and filtered to collect the precipitate using a Buchner funnel and #4 Whatman filter paper. The wet cake was washed with 1.5 L of deionized water. The washed precipitate was dried overnight in a vacuum oven under 15-20" Hg and at a temperature of 90° C. The weight of dry thiabendazole crystals was 38.0 g, which corresponds to a yield of 75.5%. The purity was determined to be 99.67% (based on area %) using HPLC analysis.

An additional 3.7 g (7.4%) of thiabendazole were recovered by adding 200 ml of fresh deionized water to the mother liquor filtrate. The crystals were filtered on #4 Whatman filter paper, washed with fresh deionized water and dried.

EXAMPLE 16

Synthesis of thiabendazole using $ZnCl_2$ as the acid catalyst

To a 500 ml four-neck, round-bottom flask fitted with a mechanical stirrer, thermometer with $N_2$ inlet and a condenser equipped with a water scrubber (200 ml of water) were charged 160 ml of 1-butanol and 0.1 g ($5.7 \times 10-4$ mole) of ascorbic acid. The entire assembly was flushed with $N_2$ and a $N_2$ sweep was maintained on the system for the duration of the reaction. Following this, 54 g (0.5 mole) of o-phenylenediamine, 55 g (0.5 mole) of 4-cyanothiazole and 3 g (0.02 mole) of zinc chloride were charged to the reaction vessel. The mixture was heated to reflux, 127° C. and after 4 hours the reflux temperature decreased to 121° C. After 8 hours at reflux, the reaction was determined to be complete via gas chromatography. The same procedure as the described in Example 1 was used to transfer, isolate and dry thiabendazole. The weight of dry thiabendazole crystals was 83.4 g, which corresponds to an 82.9% yield. The purity was determined to be 99.78% (based on area %) using HPLC analysis.

The product was purified to remove colored impurities in the following manner: To a 250 ml flask fitted with a thermometer were charged 10 g of thiabendazole, 150 ml of deionized water and 6 ml of 38% hydrochloric acid. The mixture was heated to dissolve thiabendazole and when the pot temperature reached 85° C., 1 g of Norit carbon was added. After stirring for 15 minutes at 85° C., the mixture was hot-filtered to remove carbon. The pH of the filtered solution was adjusted to a value of 8 by adding 5 ml of 28% ammonium hydroxide. After cooling to room temperature, the deposited thiabendazole crystals were filtered, washed with 600 ml of deionized water and dried in a vacuum oven at 90° C. The off-white thiabendazole crystals recovered weighed 8.73 g.

EXAMPLE 17

Synthesis of thiabendazole using $SnCl_2.2H_2O$ as the acid catalyst

To a 500 ml four-neck, round-bottom flask fitted with a mechanical stirrer, thermometer with $N_2$ inlet and a condenser equipped with a water scrubber (200 ml of water) were charged 285 ml of 1-butanol and 0.1 g ($5.7 \times 10-4$ mole) of ascorbic acid. The entire assembly was flushed with $N_2$ and a $N_2$ sweep was maintained on the system for the duration of the reaction. Next, 54 g (0.5 mole) of o-phenylenediamine, 55 g (0.5 mole) of 4-cyanothiazole and 2 g (0.01 mole) of tin(II)chloride dihydrate were charged to the reaction vessel. The mixture was heated to reflux, 124° C., and after 4 hours the reflux temperature decreased to 122° C. After 8 hours at reflux, the reaction was determined to be complete via gas chromatography. The reaction mass was cooled to room temperature and the same procedure as that described in Example 1 was used to isolate and dry thiabendazole. The weight of dry thiabendazole crystals was 75.0 g, which corresponds to a 74.5% yield. The purity was determined to be 99.77% (based on area %) using HPLC analysis.

A portion of the product, 10 g, was purified to remove colored impurities using the same treatment described in Example 16. The white thiabendazole crystals recovered weighed 8.10 g.

EXAMPLE 18

Synthesis of thiabendazole using anhydrous methanesulfonic acid as the acid catalyst To a 500 ml four-neck, round-bottom flask fitted with a mechanical stirrer, thermometer with $N_2$ inlet and a condenser equipped with a water scrubber (200 ml of water) were charged 160 ml of 1-butanol and 0.1 g ($5.7 \times 10-4$ mole) of ascorbic acid. The entire assembly was flushed with $N_2$ and a $N_2$ sweep was maintained on the system for the duration of the reaction. Following this, 54 g (0.5 mole) of o-phenylenediamine and 55 g (0.5 mole) of 4-cyanothiazole were charged to the reaction vessel. Next, 26 ml (0.39 mole) of methanesulfonic acid were added dropwise to the reaction vessel and a 20° C. rise in the room temperature mixture was observed. Subsequently, the mixture was heated to reflux, 127.5° C., and after 2 hours the reflux temperature decreased to 120° C. After 6 hours at reflux, the reaction was determined to be complete via gas chromatography. The same procedure as that described in Example 1 was used to transfer, isolate and dry thiabendazole. The weight of dry thiabendazole crystals was 87.60 g, which corresponds to an 87.1% yield. The purity was determined to be 99.84% (based on area %) using HPLC analysis.

EXAMPLE 19

Synthesis of thiabendazole using anhydrous acetic acid as the acid catalyst

To a 500 ml four-neck, round-bottom flask fitted with a mechanical stirrer, thermometer with $N_2$ inlet and a condenser equipped with a water scrubber (200 ml of water) were charged 75 ml of 1-butanol and 0.05 g ($2.8 \times 10-4$ mole) of ascorbic acid. The entire assembly was flushed with $N_2$ and a $N_2$ sweep was maintained on the system for the duration of the reaction. Following this, 27 g (0.25 mole) of o-phenylenediamine, 27.5 g (0.25 mole) of 4-cyanothiazole, and 13 ml (0.23 mole) of acetic acid were charged to the reaction vessel. The mixture was heated to reflux, 121° C., and after 8 hours at reflux the reaction was determined to be complete via gas chromatography. The reaction mass was cooled to room temperature and 20 ml of 1-butanol were added to thin the reaction mixture. The same procedure as that described in Example 1 was used to isolate and dry thiabendazole. The weight of dry thiabendazole crystals was 37.92 g, which corresponds to a 75.4% yield. The purity was determined to be 99.73% (based on area %) using HPLC analysis.

EXAMPLE 20

Synthesis of thiabendazole using ammonium chloride as the acid catalyst

To a 500 ml four-neck, round-bottom flask fitted with a mechanical stirrer, thermometer with $N_2$ inlet and a condenser equipped with a water scrubber (200 ml of water) were charged 90 ml of 1-butanol and 0.05 g ($2.8 \times 10-4$ mole) of ascorbic acid. The entire assembly was flushed with $N_2$ and a $N_2$ sweep was maintained on the system for the duration of the reaction. Following this, 27 g (0.25 mole) of o-phenylenediamine, 27.5 g (0.25 mole) of 4-cyanothiazole and 4 g (0.075 mole) of ammonium chloride were charged to the reaction vessel. The mixture was heated to reflux, 126° C. and after 5 hours the reflux temperature decreased to 121° C. After 8 hours at reflux the reaction was determined to be complete via gas chromatography. The reaction mass was cooled to room temperature and 40 ml of 1-butanol were added to thin the reaction mixture. The mixture was filtered and the precipitate was washed with two 50 ml portions of 1-butanol, followed by, three 100 ml portions of deionized water. The same procedure as that described in Example 1 was used to dry thiabendazole. The weight of dry thiabendazole crystals was 42.4 g, which corresponds to a 84.3% yield. The purity was determined to be 99.68% (based on area %) using HPLC analysis.

EXAMPLE 21

Synthesis of thiabendazole using sulfamic acid as the acid catalyst

To a 500 ml four-neck, round-bottom flask fitted with a mechanical stirrer, thermometer with $N_2$ inlet and a condenser equipped with a water scrubber (200 ml of water) were charged 75 ml of 1-butanol and 0.05 g ($2.8 \times 10-4$ mole) of ascorbic acid. The entire assembly was flushed with $N_2$ and a $N_2$ sweep was maintained on the system for the duration of the reaction. Following this, 27 g (0.25 mole) of o-phenylenediamine and 27.5 g (0.25 mole) of 4-cyanothiazole were charged to the reaction vessel. The mixture was heated to 50° C. and 10 g (0.1 mole) of sulfamic acid were added. Refluxing commenced at 126° C. and after 2 hours the reflux temperature of the reaction mixture decreased to 121° C. After 5 hours at reflux the reaction was determined to be complete via gas chromatography. The reaction mass was cooled to 10° C. and filtered. The cake was washed with two 50 ml portions of 1-butanol, followed by, three 200 ml portions of deionized water. The product, thiabendazole was dried using the conditions described in Example 1. The weight of dry thiabendazole crystals was 38.1 g, which corresponds to a 75.7% yield. The purity was determined to be 99.72% (based on area %) using HPLC analysis.

The data for Examples 16 to 21 is summarized in Table IV.

TABLE IV

Synthesis of Thiabendazole In 1-Butanol Using Other Acid Catalysts

| Acid Catalyst | Mole Ratio OPD:Acid | Rxn Time (hrs.) | % Yield | % Purity (HPLC area %) |
|---|---|---|---|---|
| Zinc Chloride | 1.0:0.04 | 8 | 82.9 | 99.78 |
| Tin(II)Chloride dihydrate | 1.0:0.02 | 8 | 74.5 | 99.77 |
| Methanesulfonic Acid | 1.0:0.78 | 6 | 87.1 | 99.84 |
| Acetic Acid | 1.0:0.91 | 8 | 75.4 | 99.73 |
| Ammonium Chloride | 1.0:0.30 | 8 | 84.3 | 99.68 |
| Sulfamic Acid | 1.0:0.41 | 5 | 75.7 | 99.72 |

EXAMPLE 22

The multiple runs described below illustrate an important aspect of the preferred embodiment of the present invention, i.e., the fact that the 1-butanol mother liquor and 1-butanol washes can be combined and recycled to the reaction vessel. This can be done repeatedly without adversely affecting the yield or purity of thiabendazole.

Run 1: Thiabendazole was prepared as in Example 1 with the exception that the amount of 20 degree Be' hydrochloric acid added dropwise was 46.0 ml (0.47 mole). The reaction produced 87.0 g of thiabendazole corresponding to an 86.5% yield with 99.85% purity (based on HPLC % area). The mother liquor and 1-butanol wash filtrates were saved.

Run 2: The saved filtrates were combined in the following manner to provide a total volume of 285 ml: all of the mother liquor (130 ml), all of the first 1-butanol wash (77 ml), and 78 ml of the second 1-butanol wash. The combined filtrates replaced fresh 1-butanol as the reaction medium for Run 2. Thiabendazole was prepared as in Run 1 in a 90.8% yield (91.4 g) and 99.82% purity (based on HPLC % area). The mother liquor and 1-butanol wash filtrates from this run were saved.

Run 3: The saved filtrates were combined in the following manner to provide a total volume of 285 ml: all of the mother liquor (166 ml), all of the first 1-butanol wash (91 ml), and 28 ml of the second 1-butanol wash. The combined filtrates served as the reaction medium for Run 3. Thiabendazole was prepared as in Run 1 in an 88.1% yield (88.7 g) and 99.81% purity (based on HPLC % area). The mother liquor and 1-butanol wash filtrates from this run were saved.

Run 4: The saved filtrates were combined in the following manner to provide a total volume of 285 ml: all of the mother liquor (142 ml), all of the first 1-butanol wash (68 ml), and 75 ml of the second 1-butanol wash. The combined filtrates served as the reaction medium for Run 4. Thiabendazole was prepared as in Run 1 in an 89.4% yield (90.0 g) and 99.78% purity (based on HPLC % area). The mother liquor and 1-butanol was filtrates from this run were saved.

Run 5: The saved filtrates were combined in the following manner to provide a total volume of 285 ml: all of the mother liquor (137 ml), all of the first 1-butanol wash (87 ml), and 61 ml of the second 1-butanol wash. The combined filtrates served as the reaction medium for Run 5. Thiabendazole was prepared as in Run 1 in a 90.5% yield (91.1 g) and 99.76% purity (based on HPLC % area).

We claim:

1. A process for preparing thiabendazole which comprises reacting 4-cyanothiazole with (a) o-phenylenediamine in the presence of an acid catalyst, or (b) a protonic acid salt of o-phenylenediamine, at a temperature in the range between 85° and 145° C. in a liquid polar organic compound for a time sufficient to effect the desired conversion to thiabendazole, and recovering thiabendazole from the reaction mass; said polar organic compound being a liquid in which thiabendazole is substantially insoluble, and 4-cyanothiazole, said catalyst, o-phenylenediamine, and protonic acid salts of o-phenylenediamine, are soluble, and being selected from alkanols containing 3 to 8 carbon atoms, alkanediols containing 2 to 8 carbon atoms, alkane polyethers containing 4 to 10 carbon atoms and 2 to 4 oxygen oxygen atoms, and alkoxyalkanols having 1 to 8 carbon atoms in the alkoxy group and 1 to 8 carbon atoms in the alkanol portion of the molecule.

2. The process of claim 1 wherein said reaction temperature is between about 90° C. and about 140° C.

3. The process of claim 1 wherein the mole ratio of o-phenylenediamine to 4-cyanothiazole ranges between 1:0.9 and 1:1.1.

4. The process of claim 1 wherein said liquid polar organic compound is 1-propanol, 1-butanol, 2-butanol, 2-methyl-1-propanol, 3-methyl-1-butanol, 2-ethyl-1-hexanol, cyclohexanol, 1,2-ethanediol, 1,2-propanediol, 1,3-propanediol, 1,5-pentanediol, 1,4-dioxacyclohexane, 1,1'-oxybis[2-methoxyethane], 2,5,8,11-tetra-oxadodecane, 2-methoxyethanol, or 2-ethoxyethanol.

5. The process of claim 1 wherein said acid catalyst is hydrochloric acid, hydrobromic acid, ammonium chloride, ammonium bromide, ammonium acetate, ammonium phosphate, ammonium nitrate, sulfamic acid, zinc chloride, stannous chloride, aluminum chloride, acetic acid, oxalic acid, propionic acid, adipic acid, methanesulfonic acid, benzenesulfonic acid, or p-toluenesulfonic acid.

6. The process of either of claims 1, 2, or 3 wherein said polar organic compound is 1-butanol and said catalyst is HCl.

7. A process for preparing thiabendazole comprising: (a) contacting o-phenylenediamine with an acid catalyst in a polar organic solvent; (b) reacting the reaction mixture at its boiling point with 4-cyanothiazole at a mole ratio of o-phenylenediamine to 4-cyanothiazole in the range between 1:0.9 and 1:1.1 for a time sufficient to effect the desired conversion to thiabendazole; (c) isolating precipitated thiabendazole from the mother liquor which comprises solubilized impurities; (d) washing said solid thiabendazole with an additional quantity of said polar organic solvent and then with water, thereby obtaining a white solid of high purity, and (e) recycling said polar organic solvent wash and recovered mother liquor to said reactor; said polar organic compound being a liquid in which thiabendazole is substantially insoluble and o-phenylenediamine, protonic acid salts of o-phenylenediamine, 4-cyanothiazole and said catalyst are soluble, and being selected from alkanols containing 3 to 8 carbon atoms, alkanediols containing 2 to 8 carbon atoms, alkane polyethers containing 4 to 10 carbon atoms and 2 to 4 oxygen oxygen atoms, and alkoxyalkanols having 1 to 8 carbon atoms in the alkoxy group and 1 to 8 carbon atoms in the alkanol portion of the molecule.

8. The process of claim 7 wherein the reaction temperature is between about 90° C. to about 140° C.

9. The process of claim 7 wherein said polar organic compound is 1-propanol, 1-butanol, 2-butanol, 2-methyl-1-propanol, 3-methyl-1-butanol, 2-ethyl-1-hexanol, cyclohexanol, 1,2-ethanediol, 1,2-propanediol, 1,3-propanediol, 1,5-pentanediol, 1,4-dioxacyclohexane, 1,1'-oxybis[2-methoxyethane], 2,5,8,11-tetra-oxadodecane, 2-methoxyethanol, or 2-ethoxyethanol.

10. The process of claim 7 wherein said acid catalyst is hydrochloric acid, hydrobromic acid, ammonium chloride, ammonium bromide, ammonium acetate, ammonium phosphate, ammonium nitrate, sulfamic acid, zinc chloride, stannous chloride, aluminum chloride, acetic acid, oxalic acid, propionic acid, adipic acid, methanesulfonic acid, benzenesulfonic acid, or p-toluenesulfonic acid.

11. The process of claim 7 wherein said acid catalyst is in the form of an aqueous solution when it is contacted with o-phenylenediamine, and a portion of the water in the reaction mixture is removed by distillation prior to reacting the resulting mixture with 4-cyanothiazole.

12. The process of either claim 7, 8 or 11 wherein said polar organic compound is 1-butanol and said catalyst is HCl.

* * * * *